United States Patent [19]

Benovic et al.

[11] Patent Number: 4,608,336

[45] Date of Patent: Aug. 26, 1986

[54] #3B THEOPHYLLINE IMMUNOASSAY EMPLOYING 9-THEOPHYLLINE REAGENTS

[75] Inventors: Jeffrey L. Benovic, Durham, N.C.; Robert T. Buckler, Edwardsburg, Mich.; John F. Burd, Elkhart, Ind.; Thomas M. Li, Elkhart, Ind.

[73] Assignee: Miles Laboratories, Inc., Elkhart, Ind.

[21] Appl. No.: 493,609

[22] Filed: May 11, 1983

Related U.S. Application Data

[62] Division of Ser. No. 296,817, Aug. 27, 1981, Pat. No. 4,533,493.

[51] Int. Cl.$^4$ ............................................ G01N 33/53
[52] U.S. Cl. ........................................ 435/7; 435/18; 435/805; 435/810; 436/518; 436/536; 436/544; 436/808; 436/810; 436/815; 436/822; 436/823

[58] Field of Search ................. 435/7, 14, 18, 805, 435/810; 436/518, 536, 544, 808, 810, 815, 822, 823

[56] References Cited

U.S. PATENT DOCUMENTS

| | | | |
|---|---|---|---|
| 4,262,089 | 4/1981 | Singh et al. | 435/7 |
| 4,279,992 | 7/1981 | Boguslaski et al. | 435/7 |
| 4,302,438 | 11/1981 | Zech | 436/815 |

Primary Examiner—Esther M. Kepplinger
Attorney, Agent, or Firm—Andrew L. Klawitter

[57] ABSTRACT

Immunoassay method and reagent means for determining theophylline in biological fluids such as serum. The antibody employed in the method is prepared from an immunogen comprising theophylline coupled at its 9-position to an immunogenic carrier material.

12 Claims, No Drawings

#3B THEOPHYLLINE IMMUNOASSAY EMPLOYING 9-THEOPHYLLINE REAGENTS

This is a division of application Ser. No. 296,817, filed Aug. 27, 1981, now U.S. Pat. No. 4,533,493.

BACKGROUND OF THE INVENTION

1. Field of the Invention

This invention relates to novel theophylline derivatives pertaining to immunoassays for determining theophylline in liquid media such as biological fluids. Such derivatives include theophylline-immunogens used to stimulate production of antibodies to theophylline in host animals by conventional techniques. Also provided are labeled theophylline conjugates used as reagents, along with the theophylline antibodies, in particularly preferred immunoassays. Intermediates in the synthesis of the aforementioned immunogens and labeled conjugates are also provided.

Theophylline [1,3-dimethylxanthine, cf. *The Merck Index*, 9th ed., p. 1196(1976)] is a drug of great value in the management of asthmatic patients. The drug is used prophylactically, as an adjunct in the treatment of prolonged asthmatic attacks and in the management of status asthmaticus [Goodman and Gilman, *The Pharmacological Basis of Therapeutics*, 5th ed., MacMillan (New York 1975) p. 375]. However, because of its potential toxicity, proper dosage administration is critical. Frequent testing of serum or plasma concentrations assists in maintaining therapeutic levels and avoiding toxic levels.

2. Description of the Prior Art

The determination of theophylline by immunoassay is well known. Commercial test kits are available for measuring serum and plasma theophylline levels by radioimmunoassay, enzyme immunoassay, and substrate-labeled fluorescent immunoassay. Radioimmunoassays for determining theophylline are described by Cook et al, *Res. Commun. Chem. Path. Pharm.* 13:497(1976), Nishikawa et al, *Chem. Pharm. Bull.* 27:893(1979), and German No. OLS 2,901,281. Reagents for use in an enzyme immunoassay for determining theophylline are described in U.S. Pat. No. 4,230,805. The determination of theophylline by substrate-labeled fluorescent immunoassay (SLFIA) is described in U.S. Pat. No. 4,279,992. See also British Pat. No. 1,552,607 and Li et al, *Clin. Chem.* 27:22(1981).

Theophylline immunogens have been prepared by coupling the drug at various positions on its ring structure to conventional immunogenic carrier materials. Immunogens prepared by derivatization of theophylline at its 8-position are described by Cook et al and Li et al, supra, and in U.S. Pat. No. 4,279,992. Derivatization at the 7-position is known from Nishakawa et al supra, and German No. OLS 2,901,218. U.S. Pat. No. 4,230,805 describes the coupling of theophylline at its 3-position.

The state-of-the-art of preparing antibodies to haptens such as drugs is represented by Weinryb et al, *Drug Metabolism Reviews* 10:271(1979); Playfair et al, *Br. Med. Bull.* 30:24(1974); Broughton et al, *Clin. Chem.* 22:726(1976); and Butler, *J. Immunol. Meth.* 7:1(1975). The preparation of 9-xanthine derivatives are described by Lister, Purines, Wiley, Interscience (New York 1971) pp. 223–228; Hurst, *An Introduction to the Chemistry and Biochemistry of the Pyrimidines, Purines, and Pteridines*, John Wiley & Sons (New York 1980) p. 66; Rybar et al, *Collect. Czech. Chem. Commun.* 37:3936(1972); Fleiderer and Nubel, *Justus Liebig's Annalen* 631:168(1960); von Schuk, German Pat. No. 1,113,696 (*Chem. Abst.* 56P: 12910e); and Blicke and Schaff, *J. Amer. Chem. Soc.* 78:5857(1956).

SUMMARY OF THE INVENTION

The present invention uniquely provides reagents for use in theophylline immunoassays involving the coupling to or derivatization of the drug at the 9-position. The 9-theophylline immunogen, i.e., the conjugate formed by covalently linking theophylline at its 9-position to an immunogenic carrier material, is used to prepare antibodies to theophylline which have advantageous cross-reactivity characteristics. The theophylline antibodies of the present invention cross-react insignificantly with the major theophylline analogs and metabolites present in biological fluids, namely, caffeine (1,3,7-trimethylxanthine), 3-methylxanthine, 1,7-dimethylxanthine, 3,7-dimethylxanthine, and theobromine. In particular, the present theophylline antibodies possess an unexpectedly extremely low cross-reactivity for the most troublesome potential interferant in biological fluids, caffeine, compared to the antibodies obtained from the known, closely analogous, 7-theophylline and 8-theophylline immunogens, supra.

In a preferred embodiment, the present invention provides novel intermediates in the preparation of the 9-substituted theophylline reagents. Also provided are an improved immunoassay method and reagent means for the determination of theophylline with the use of the novel antibodies of the present invention. The present invention also provides labeled theophylline conjugates for particularly preferred embodiments of such immunoassay.

DESCRIPTION OF THE PREFERRED EMBODIMENTS

The present invention, in all of its interrelated embodiments, is focused on preparation of 9-substituted theophylline derivatives which can then be used to form immunogens by coupling them to conventional carrier materials, and subsequently used to obtain theophylline antibodies, or can be used to form labeled conjugates which serve as the detectable reagents in theophylline immunoassays.

9-THEOPHYLLINE IMMUNOGENS

The present immunogens have the general formula:

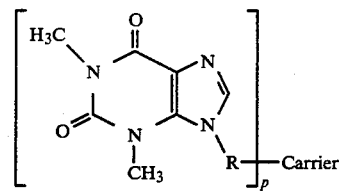

wherein R is an appropriate linking group, Carrier is a conventional immunogenic carrier material, and p is the number of theophylline moieties conjugated to the carrier. The number p is sometimes referred to as the epitopic density of the immunogen and in the usual situation will be on the average from 1 to about 50, more normally from 1 to about 25. Optimal epitopic densities, considering the ease and reproducibility of synthesis of the immunogen and antibody response, fall between about 2 and about 20, more usually between 5 and 15.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds,* Prentice-Hall (Englewood Cliffs, N.J. U.S.A., 1976); Butler, *J. Immunol. Meth.* 7:1–24 (1975); Weinryb and Shroff, *Drug Metab. Rev.* 10:271–283 (1975); Broughton and Strong, *Clin. Chem.* 22:726–732 (1976); and Playfair et al, *Br. Med. Bull* 30:24–31 (1974).

Appropriate 9-theophylline derivatives are couplable to immunogenic carrier materials according to well known techniques. For example, 9-carboxylated theophylline derivatives can be coupled to immunogenic carriers having amino groups by standard peptide bond-forming reactions such as described in *Peptides,* ed. Goodman and Meienhofer, John Wiley & Sons (New York 1977) p. 6 et seq. 9-Thiolated theophylline derivatives can be attached to carriers having thiol groups by the disulfide interchange reaction [Martin et al, *Biochem.* 20:4229 (1981)]. Alternatively, a third group can be introduced into one of the reactants and a maleimido group into the other and the two coupled together in a manner similar to that described by Liu et al, *Biochem.* 18:690 (1979). 9-Aminated theophylline derivatives can be coupled to carriers having carboxyl groups by amide bond-forming reactions such as those involving carbodiimides [Aherne et al, *Brit. J. Clin. Pharm.* 3:561 (1976)], mixed anhydrides [Erlanger et al, *Methods in Immunology and Immunochemistry,* ed. Williams and Chase, Academic Press (New York 1967) p. 149], and the acid azide and active ester reactions [Kopple, *Peptides and Amino Acids,* W. A. Benjamin (New York 1966). See also *Clin. Chem.* 22:726 (1976). Similarly, the amino theophylline derivatives can be coupled to carriers having amino groups using conventional bifunctional reagents such as bis-isocyanates, bis-imidoesters, and glutaraldehyde *Immunochem.* 6:53 (1969)]. See also Kopple, supra, and Lowe and Dean, *Affinity Chromatography,* John Wiley & Sons (New York 1974). A multitude of other coupling techniques are available to those of ordinary skill in the art for joining the various 9-theophylline derivatives of the present invention with conventional immunogenic carrier materials.

Particularly preferred are the theophylline immunogens of the formula

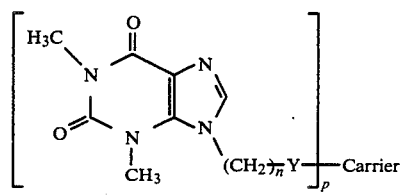

wherein Y is an amide group, ie., —NHCO—, Carrier is an immunogenic protein or polypeptide, n is an integer from 1 through 10, and p is on the average from 1 to the number of available amide coupling sites on the carrier material, and preferably is as defined above. The amide coupling group may be oriented in either of the two possible ways, with the nitrogen atom in the amide group being from carrier amino groups and the carbon atom being from an appropriate theophylline derivative (e.g., a carboxylic acid):

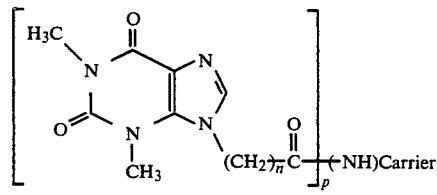

with p then representing the average number of coupled amino groups in the carrier (and preferably is as defined above), or with the nitrogen atom being from an appropriate theophylline derivative (e.g., an amino derivative) and the carbon atom being from carrier carboxyl groups;

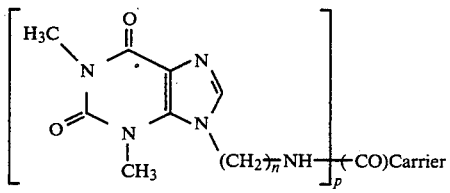

with p then representing the average number of coupled carboxyl groups in the carrier (and preferably is again as defined above).

THEOPHYLLINE ANTIBODIES

Preparation of specific antibodies using the present immunogen conjugates may follow any conventional technique. Numerous texts are available describing the fundamental aspects of inducing antibody formation, for example reference may be made to Parker, *Radioimmunoassay of Biologically Active Compounds,* Prentice-Hall (Englewood Cliffs, N.J., U.S.A., 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hydridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266:495 (1977), and *Science* 208:692 (1980).

9-SUBSTITUTED THEOPHYLLINE DERIVATIVES

A wide variety of synthetic routes are available to one skilled in the art for derivatizing theophylline at its 9-position and coupling the derivative to the carrier. Following are descriptions of some such synthetic routes.

2,6-Dioxopurines can exist in two isomeric forms which are known by the trivial names xanthines [3,7-dihydro-1H-purine-2,6-dione (1)] and iso-xanthines [3,9-dihydro-1H-purine-2,6-dione (2)] and are numbered as shown in formula 1.

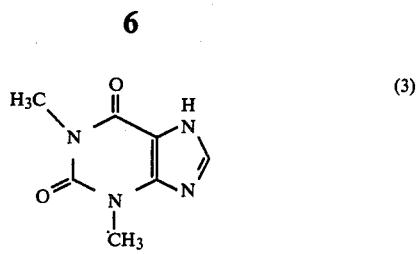

primarily yields $N^7$-derivatives, with only small amounts of the $N^9$-derivatives being formed [Lister, *Purines*, Wiley, Interscience (New York 1971) pp. 223–228]. Accordingly, 9-substituted derivatives are usually prepared by a variation of the Traube synthesis by attaching the desired substituent to the nitrogen atom destined to occupy the 9-position [Hurst, *An Introduction to the Chemistry and Biochemistry of the Pyrimidines, Purines, and Pteridines*, John Wiley & Sons (New York 1980) p. 66].

For example, with reference to Diagram A, 9-(2-hydroxyethyl)theophylline (7) is prepared by reacting 6-chloro-1,3-dimethyluracil (4) with 2-aminoethanol to give the uracil (5). This is nitrosated and reduced to give the diamino uracil (6), which upon treatment with formic acid yields the 9-substituted theophylline derivative (7). See Rybar et al, *Collect. Czech. Chem. Commun.* 37:3936(1972).

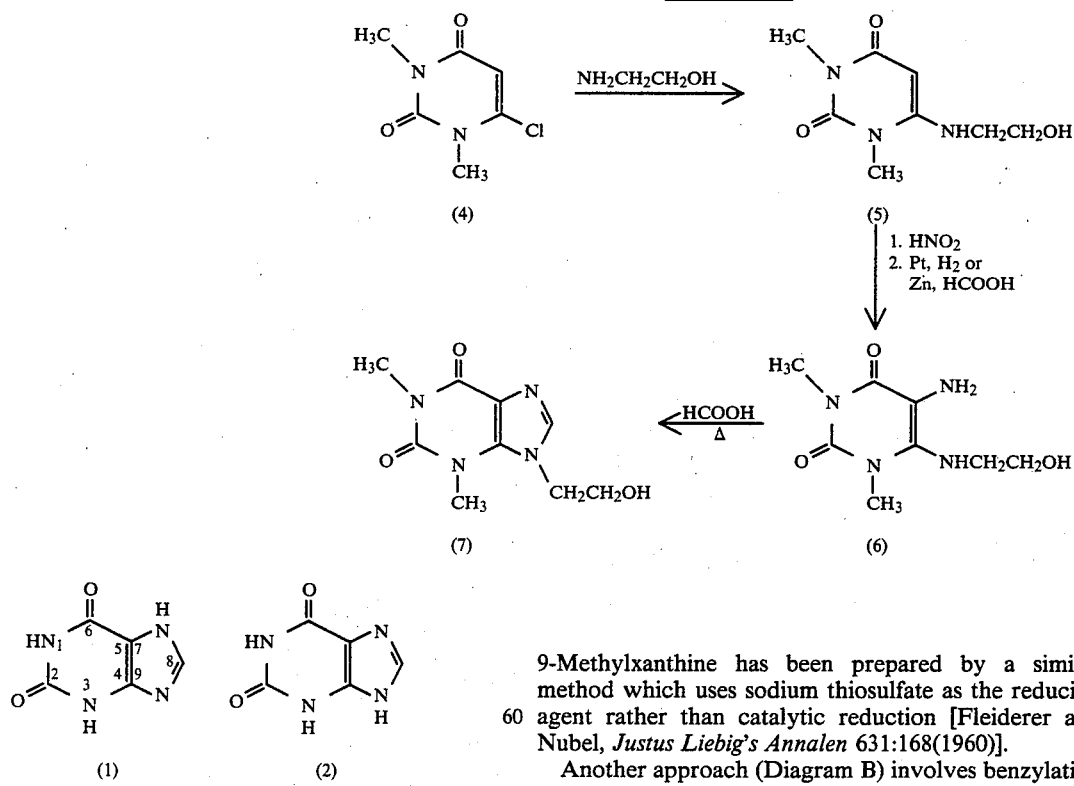

Diagram A

According to this trivial nomenclature, the 9-substituted theophylline derivatives and conjugates of the present invention are in fact 9-substituted iso-xanthines. Direct alkylation of 1,3-dimethylxanthine [theophylline, (3)]

9-Methylxanthine has been prepared by a similar method which uses sodium thiosulfate as the reducing agent rather than catalytic reduction [Fleiderer and Nubel, *Justus Liebig's Annalen* 631:168(1960)].

Another approach (Diagram B) involves benzylation of 1,3-dimethylxanthine (8) at the 7-position to yield product (9) which is then alkylated with dialkylsulfate ($R^1$=alkyl) to yield the ionic intermediate (10). Catalytic removal of the benzyl group leads to 9-alkyl theophylline (11). See von Schuk, German Pat. No. 1,113,696 (*Chem. Abst.* 56P:12910e).

Diagram B

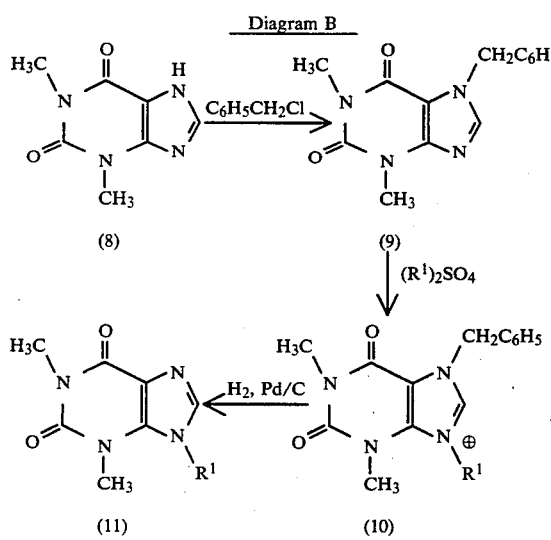

Still another approach (Diagram C) involves reaction of 5,6-diaminouracil (12) with an alkyl isothiocyanate ($R^2$=alkyl) to yield the thiourea (13). This is cyclized to the 8-mercapto derivative (14) which is then desulfurized with Raney nickel to give 9-alkylated theophyllines (15). See Blicke and Schaff, *J. Amer. Chem. Soc.* 78:5857(1956).

Diagram C

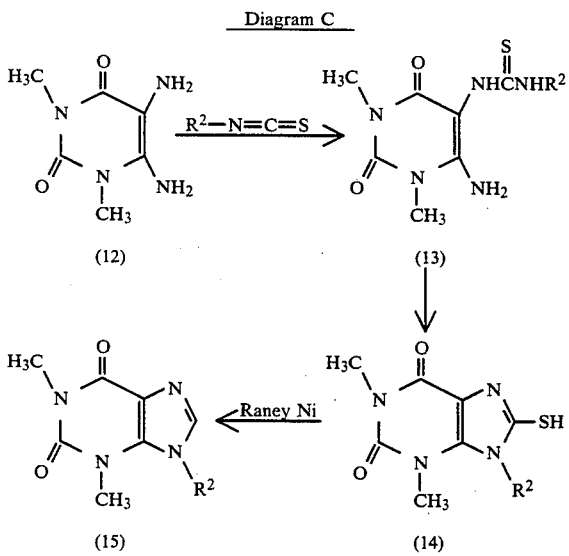

Based on the above-described synthetic routes, it is clear that 9-functionalized theophylline derivatives (16)

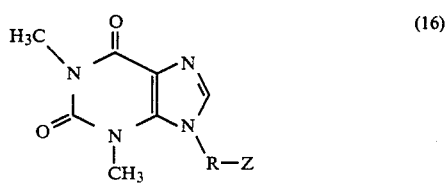

where Z is a reactive group for coupling to the immunogenic carrier material or an appropriate labeling residue (e.g., Z can be amino, carboxyl, hydroxyl, mercapto, or maleimido), can be prepared with a wide latitude in the nature of the linking group R.

For example, in the method of Diagram A, 2-aminoethanol can be replaced by the general reagent $H_2N$—R—Z provided R is stable to treatment with formic acid and Z is compatible with a primary amino group. In the method of Diagram B, the dialkylsulfate is replaced by the general reagent $(Z—R)_2$—$SO_4$ provided R and Z are not reactive with the organic sulfate. Likewise, in the method of Diagram C, the alkyl isothiocyanate is replaced by the general reagent Z—R—N=C—S, provided R and Z are not reactive with the isothiocyanate group. Thus, one skilled in the art has a wide variety of linking groups R that can be introduced to the derivatives of the present invention. Exemplary of such choices are linear and branched alkylenes comprising from 1 to as many as 15, more usually 10 or less, and normally less than 6, carbon atoms (e.g., methylene, ethylene, n-propylene, iso-propylene, n-butylene, and so forth). In addition, such alkylenes can contain other substituents such as cyano, amino (including substituted amino), acylamino, halogen, thiol, hydroxyl, carbonyl groups, carboxyl (including substituted carboxyls such as esters, amides, and substituted amides). The linking group R can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, amino, thio ether, amidino, sulfone, or sulfoxide. Also, such linkages can include unsaturated groupings such as olefinic or acetylenic bonds, imino, or oximino groups. Preferably R will be a chain, usually an aliphatic group, comprising between 1 and 20 atoms, more usually between 1 and 10, excluding hydrogen, of which between 0 and 5 are heteroatoms selected from nitrogen, oxygen, and sulfur. Particularly preferred are the derivatives wherein R is $-(CH_2)_n-$ with n being an integer from 1 through 10 and wherein Z is amino or carboxyl. Therefore, the choice of linking group R is not critical to the present invention and may be selected by one of ordinary skill taking normal precautions to assure that stable compounds are produced.

Similarly, the terminal functional group Z can vary widely, although amino, carboxyl, thiol, mercapto, hydroxyl, and maleimido will be preferred. Examples of synthetic routes available to obtain 9-theophylline derivatives having such preferred terminal functional groups follow:

(a) 9-(Amino-functionalized)theophylline

Following the procedure of Diagram A, 6-chloro-1,3-dimethyluracil (4) is reacted with a di-amino compound having one amino function suitably protected, such as with a tert-butyloxycarbonyl group: $NH_2$—R—$NHCOOC(CH_3)_3$ [Stahl et al, *J. Org. Chem.* 43:2285 (1978)]. The product (17) is nitrosated, reduced, and cyclized to the protected 9-substituted theophylline (18), which in turn is de-protected with acid to give the primary amino compound (19).

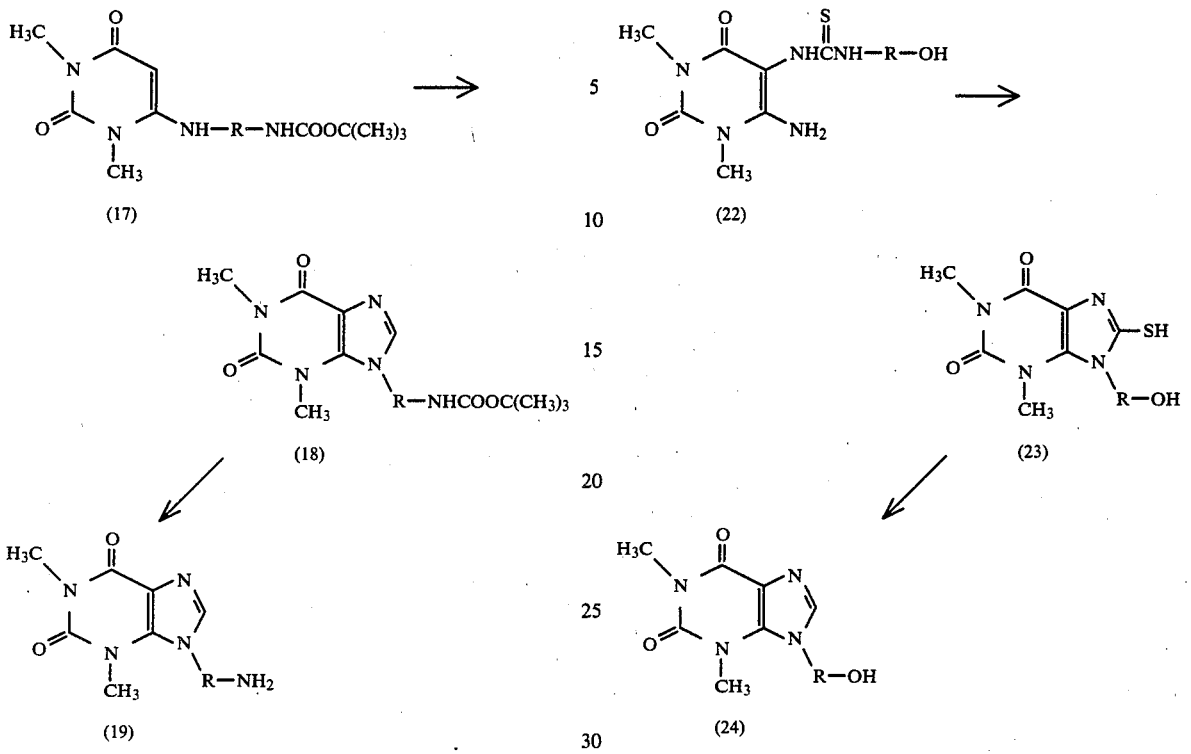

(b) 9-(Carboxyl-functionalized)theophylline

Following the procedure of Diagram A, 6-chloro-1,3-dimethyluracil (4) is reacted with a reagent of the general formula $NH_2R$—COOH to produce (20) which is converted to the 9-carboxy-modified theophylline derivative, (21) by the previously described reactions.

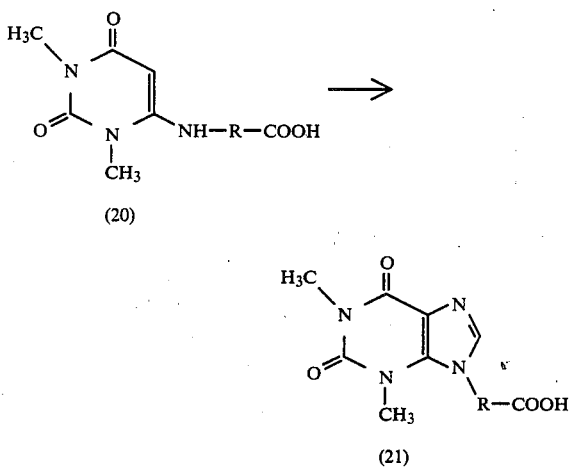

(c) 9-(Hydroxyl-functionalized)theophylline

Following the procedure of Diagram C, amino alcohols $NH_2$—R—OH are reacted with carbon disulfide to give S=C=N—R—OH and these in turn are reacted with 5,6-diamino-1,3-dimethyluracil (12) to give the thioureas (22). Cyclization of (22) leads to (23) which is then desulfurized to the alcohol derivatives (24). Compounds (24) can also be prepared by the route outlined in Diagram A using $NH_2$—R—OH in the reaction with 6-chloro-1,3-dimethyluracil.

(d) 9-(Mercapto-functionalized)theophylline

These compounds are prepared by the synthetic route outlined in Diagram A using $NH_2$—R—SH as the starting material in a manner analogous to the preparation of carboxy-modified theophyllines. Sodium thiosulfate can be used as the reducing agent in the reduction step.

(e) 9-(Maleimido-functionalized)theophylline

These compounds are prepared from the corresponding amino derivatives (19) by reaction with maleic anhydride to give intermediate (25) followed by cyclization to (26).

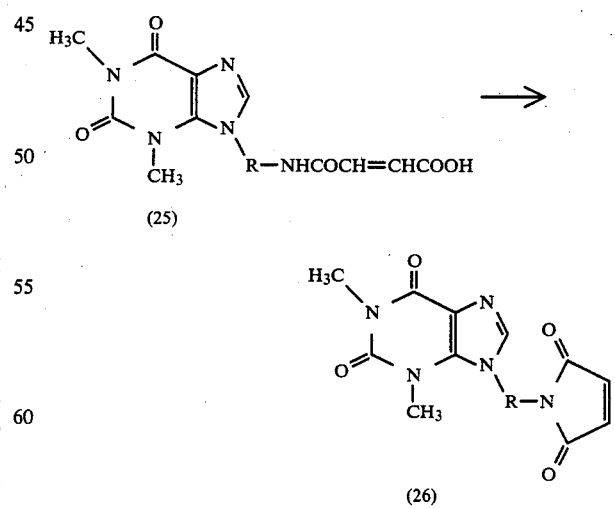

IMMUNOASSAY TECHNIQUES

The antibodies prepared from the 9-theophylline immunogens of the present invention can be used in any immunoassay method, and the corresponding reagent means, for determining theophylline, including agglutination techniques, radioimmunoassays, heterogeneous enzyme immunoassays (cf. U.S. Pat. No. 3,654,090), heterogenous fluorescent immunoassays (cf. U.S. Pat. Nos. 4,201,763; 4,171,311; 4,133,639 and 3,992,631), and homogeneous (separation-less) immunoassays. The lattermost are particularly preferred and include such techniques as fluorescence quenching or enhancement (cf. U.S. Pat. No. 4,160,016), fluorescence polarization (cf. *J. Exp. Med.* 122:1029(1965), enzyme substrate-labeled immunoassay (cf. U.S. Pat. No. 4,279,992 and U.K. Pat. Spec. 1,552,609), prosthetic group-labeled immunoassay (cf. U.S. Pat. No. 4,238,565), enzyme modulator-labeled immunoassay, e.g., using inhibitor labels (cf. U.S. Pat. Nos. 4,134,792 and 4,273,866), enzyme-labeled immunoassay (cf. U.S. Pat. No. 3,817,837), energy transfer immunoassay (cf. U.S. Pat. No. 3,996,345), chemically-excited fluorescence immunoassay (cf. U.S. Pat. No. 4,238,195) and double antibody steric hindrance immunoassay (cf. U.S. Pat. Nos. 3,935,074 and 3,998,943).

Moreover, the 9-theophylline derivatives of the present invention can be used to prepare the labeled conjugates needed to perform the various immunoassays described above. Appropriate derivatives can be radiolabeled or labeled with fluorescent moieties in accordance with standard methods. Likewise the appropriate labeling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the 9-theophylline derivatives to yield labeled conjugates.

Particularly preferred labeled conjugates are the following β-galactosyl-umbelliferone-theophylline and FAD-theophylline conjugates. The former has the formula

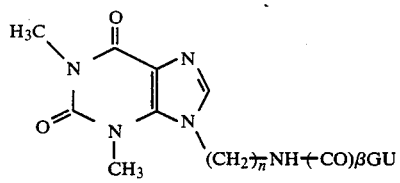

wherein $-(CO)\beta GU$ is

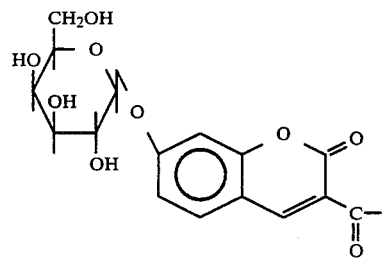

and n is an integer from 1 through 10. Such conjugates are prepared by standard peptide condensations of β-galactosyl-umbelliferone carboxylic acid (U.S. Pat. No. 4,226,978) with the appropriate 9-(aminoalkyl)theophylline.

The FAD-labeled conjugate has the formula

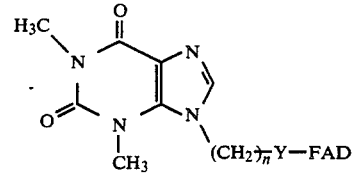

wherein FAD is flavin adenine dinucleotide or a derivative thereof, Y is an amide group, and n is an integer from 1 through 10. The amide group may be oriented in either of the two available ways and preferably is oriented with the nitrogen being from an amino group in the FAD moiety. Most preferably, the FAD moiety has the formula

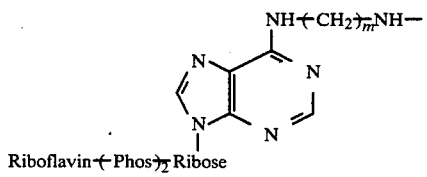

wherein Roboflavin-(-Phos-)$_2$Ribose represents the riboflavin-pyrophosphate-ribose residue in flavin adenine dinucleotide and m is an integer from 2 through 10, preferably n=5 and m=6. See also U.S. Pat. Nos. 4,213,893; 4,259,232; and 4,255,566 incorporated herein by reference.

The reagent means of the present invention comprises all of the essential chemical elements required to conduct a desired theophylline immunoassay method encompassed by the present invention. The reagent means is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired, e.g., an antibody and labeled conjugate of the present invention. Of course, the reagent means can include other materials as are known in the art and which may be desirable from a commercial and user standpoint, such as buffers, diluents, standards, and so forth. Particularly preferred is a test kit for the homogeneous competitive binding immunoassay of the present invention comprising (a) a theophylline antibody of the present invention, and (b) a labeled theophylline conjugate which has a detectable property which is altered when bound with the antibody. Also preferred is a test device comprising a reagent composition including a theophylline antibody of the present invention and a labeled theophylline conjugate which has a detectable property which is altered when bound with the antibody, and a solid carrier member incorporated with the reagent composition. The various forms of such test device are described in U.S. patent application Ser. No. 202,378, filed Oct. 30, 1980, which is incorporated herein by reference. The specific label used in the preferred test kit and test device will depend on the technique followed, as described hereinabove.

The present invention will now be illustrated, but is not intended to be limited, by the following examples:

EXAMPLE 1

Reagents

A. Preparation of 9-theophylline derivatives 9-(ω-Carboxyalkyl)-theophylline derivatives are prepared according to the following synthetic scheme (n=1–10) which is specifically exemplified below for n=5.

6-[N-(5-Carboxypentyl)amino]-1,3-dimethyl-5-formamidouracil, (IV)

A mixture of 15.8 g (0.05 mol) of the oxime (III), 200 ml of methanol, and 100 mg of platinum oxide was shaken under 4 atmospheres $H_2$ for 15 minutes at room temperature. The catalyst was removed by filtration and the filtrate concentrated under reduced pressure (35° C.) to give a red oil. Methyl formate (200 ml) was

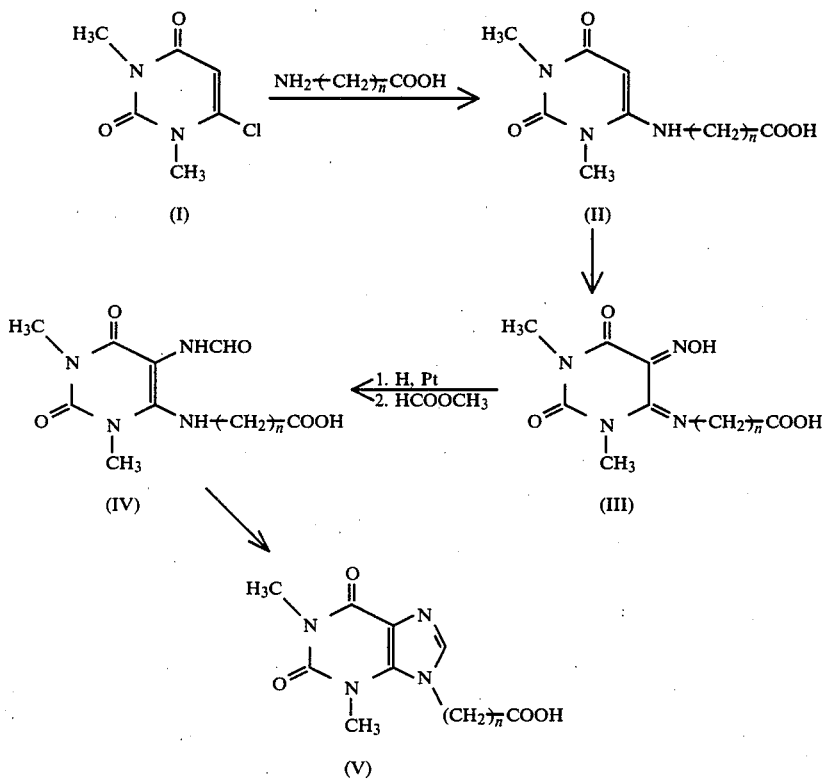

6-[N-(5-Carboxypentyl)amino]-1,3-dimethyluracil, (II), n=5

A mixture of 25 g (grams) (0.143 mol) of 6-chloro-1,3-dimethyluracil (I) (Aldrich Chemical Co., Milwaukee, WI) and 18.73 g (0.143 mol) of 6-aminocaproic acid in 100 ml (milliliters) of absolute ethanol containing 14 g (0.143 mol) of triethylamine was refluxed for 16 hours. It was cooled, evaporated under reduced pressure, and the crystalline residue recrystallized twice from $H_2O$ to give 22 g (56% yield) of the uracil derivative (II) as fine white crystals, mp 191° C.

Analysis: Calculated for $C_{12}H_{18}N_3O_4$: C, 53.52; H, 7.11; N, 15.60. Found: C, 52.78; H, 6.20; N, 15.15.

6-[N-(5-Carboxypentyl)imino]-1,3-dimethyl-5-oximino uracil, (III)

Fifteen grams (0.056 mol) of the carboxypentyl uracil (II) was suspended in 100 ml of $H_2O$ and stirred at a temperature of 50°–55° C. To this was added 7.14 g (0.084 mol) of sodium nitrite dissolved in 50 ml of $H_2O$. After one hour the reaction was cooled to 0° C., and a yellow solid removed by filtration which amounted to 11 g when dry, mp 246°–248° C. The color suggests it to be the oxime tautomer (III).

Analysis: Calculated for $C_{12}H_{18}N_4O_5$: C, 48.32; H, 6.08; N, 18.78. Found: C, 47.88; H, 6.00; N, 18.65.

added and the resulting mixture refluxed under argon for 20 hours. It was then cooled in an ice bath and the white solid collected by filtration. Recrystallization from methanol gave 9.82 g (63% yield) of the formamido uracil (IV) as white crystals, mp 152°–153° C.

Analysis: Calculated for $C_{13}H_{20}N_4O_5$: C, 49.99; H, 6.45; N, 17.94. Found: C, 49.91; H, 6.55; N, 17.67.

9-(5-Carboxypentyl)-1,3-dimethylxanthine, (V)

9.3 Grams (0.03 mol) of the formamido derivative (IV) was suspended in 500 ml of o-dichlorobenzene and stirred at reflux under an inert atmosphere for 4 hours. It was cooled and the solvent removed on a rotary evaporator attached to a vacuum pump. The crystalline residue was partitioned between 200 ml of ether and 100 ml of 5% aqueous sodium bicarbonate solution. The aqueous phase was separated, washed with 100 ml of ether, and acidified to pH 3.2 with 5N HCl. The precipitate was recrystallized first from aqueous methanol, then from absolute ethanol to give 5.8 g (66% yield) of the xanthine (V) as fine white crystals, mp 177° C.

Analysis: Calculated for $C_{13}H_{18}N_4O_4$: C, 53.05; H, 6.16; N, 19.04. Found: C, 53.48; H, 6.27; N, 18.95.

The exemplified method can be modified to yield any desired 9-(ω-carboxyalkyl)theophylline by substitution of the appropriate ω-aminoalkanoic acid for 6-aminocaproic acid in the preparation of compound (II). The corresponding 9-(ω-aminoalkyl)theophylline can be prepared by using an appropriate mono-N-blocked α,ω-diaminoalkane in place of 6-aminocaproic acid and then deblocking by conventional methods.

B. Preparation of 9-theophylline immunogen

Bovine serum albumin (200 mg; 3.0 μmol) was dissolved in 4 ml of distilled water and 150 μl (microliters) of 1N sodium hydroxide was then added to the protein solution. While vortex mixing, 3 ml of spectro-grade anhydrous dioxane was slowly added to the alkaline protein solution. The BSA solution was then placed in an ice bath. 16.8 mg (milligrams) (57.3 μmole) of 9-(5-carboxypentyl)-1,3-dimethylxanthine (Part A above) was suspended in 2 ml of dioxane. The suspension was cooled in an ice-water bath, making sure that the dioxane did not freeze. 15 μl of tri-N-butylamine was added and after mixing, 10 μl of ethyl chloroformate was also added to the cold suspension. A small magnetic bar was placed into the test tube, and the suspension was stirred in an ice-water bath using a magnetic stirrer. After 20 minutes, the activated theophylline derivative suspension was slowly added to the cold BSA solution with mixing with a magnetic stirring bar in an ice-water bath. The reaction mixture was then stirred overnight at 4° C.

The reaction mixture was brought to room temperature and chromatographed with 50 mM (millimolar) Tris buffer [tris-(hydroxymethyl)aminomethane, Calbiochem-Behring, La Jolla, Calif., U.S.A.], pH 8.2, through a 2.8×52 cm column of Sephadex G-25 (fine) (Pharmacia Fine Chemicals, Piscataway, N.J. USA) which had been equilibrated with the same buffer. Fractions of 3 ml were collected, and the absorbance at 280 nm (nanometers) monitored. The theophylline-BSA conjugate eluted in the void volume, and these fractions (30-45) were pooled. The total volume of this theophylline-BSA immunogen was measured (47 ml). The unreacted drug eluted in fractions 80 to 110.

C. Preparation of β-galactosyl-umbelliferone-theophylline conjugate

9-(5-Aminopentyl)-1,3-dimethylxanthine

A solution of 4.41 g (15 mmol) of 9-(5-carboxypentyl)-1,3-dimethyl-xanthine (V) in 100 ml of dry dimethylformamide was concentrated to 50 ml on a rotary evaporator to remove residual water. It was cooled to −5° C. in a methanol-ice bath and combined with 1.7 g (2.34 ml, 15 mmol) of triethylamine followed by 2.05 g (15 mmol) of isobutyl chloroformate. The reaction was stirred 30 minutes at −5° C., then allowed to warm to room temperature and stirred for one additional hour. It was again cooled to −5° C. and the precipitate of triethylamine hydrochloride removed by filtration. To the cold filtrate was added 2.52 g (45 mmol) of sodium azide dissolved in 20 ml of water. After stirring for 12 hours at 5° C., the reaction was diluted to 250 ml with water and extracted with 1 liter of ethyl acetate followed by 500 ml of ethyl acetate. The organic extracts were combined, dried over anhydrous magnesium sulfate, filtered, and concentrated to 250 ml on a rotary evaporator. Crystallization began to occur as the volume was reduced. Heptane (500 ml) was added to complete crystallization. After cooling for 2 hours, filtration gave 3.1 g of the intermediate 9-(5-azidocarbonylpentyl)-1,3-dimethylxanthine as fine white needles, m.p. 86° C. (eff.). This substance was not further characterized but was suspended in 150 ml of dry toluene and heated to reflux for 10 minutes while stirring under argon. The clear solution was cooled and evaporated to give an oily residue. To this was added 100 ml of 1N hydrochloric acid and this evaporated to dryness on the rotary evaporator. This left a semi-crystalline residue which was dissolved in 200 ml of hot 2-propanol containing a little methanol, filtered, and cooled in the refrigerator overnight. This deposited 2.6 g (47% yield) of the methanolate of the dihydrochloride salt of 9-(5-aminopentyl)-1,3-dimethylxanthine as fine white crystals, mp 133°–136° C.

Analysis: Calculated for $C_{13}H_{25}N_5Cl_2O_3$: C, 42.17; H, 6.80; N, 18.91. Found: C, 42.03; H, 6.88; N, 19.17.

9-[5-(7-β-Galactosylcoumarin-3-carboxamido)pentyl]-1,3-dimethylxanthine

A solution of 736 mg (2 mmol) of 7-β-galactosylcoumarin-3-carboxylic acid (U.S. Pat. No. 4,226,978) and 230 mg (2 mmol) of N-hydroxysuccinimide in 100 ml of dry dimethylformamide was concentrated to 50 ml on a rotary evaporator attached to a vacuum pump to remove last traces of water. Fifty ml of dry dimethylformamide were added and the process was repeated. The solution was then cooled to −5° C. in a methanol ice bath, and, while stirring under argon, 412 mg (2 mmol) of dicyclohexylcarbodiimide was added. The cooling bath was removed and the reaction allowed to warm to room temperature and stir for a total of 4 hours. The precipitated dicyclohexyl urea was removed by filtration. The filtrate, now containing the activated ester, was combined with 602 mg of the dihydrochloride salt of 9-(5-aminopentyl)-1,3-dimethylxanthine and 300 mg of triethylamine. After 4 hours stirring at room temperature, the reaction was diluted with 100 ml of dimethylformamide, 20 g of silica gel and 168 mg of sodium bicarbonate added, and the dimethylformamide removed under high vacuum. The impregnated silica gel was placed atop a column of 200 g of silica gel made up in chloroform. The column was eluted with a gradient of 1060 ml chloroform to 2 liters of methanol; 20 ml fractions were collected.

Fractions 88 to 108 were pooled and evaporated. The solid residue was recrystallized from methanol to give 710 mg (55% yield) of the β-galactosyl-umbelliferone-theophylline conjugate as fine white crystals, mp 168°–169° C.

Analysis: Calculated for $C_{28}H_{33}N_5O_{11} \cdot CH_3OH$: C, 53.78; H, 5.76; N, 10.81. Found: C, 52.45; H, 5.69; N, 10.76.

D. Preparation of FAD-theophylline conjugate

A solution of 736 mg (2.5 mmol) of 9-(5-carboxypentyl)-1,3-dimethylxanthine (V) in 5 ml of dry dimethylformamide was stirred under argon at −5° C. To this was added 0.35 ml (2.5 mmol) of isobutyl chloroformate. After 20 minutes at this temperature, the white precipitate of triethylammonium chloride was filtered out. The cold filtrate, now containing the mixed anhydride, was added dropwise with stirring for 30 minutes to a 0° C. solution of 1.12 g (2.5 mmol) of $N^6$-(6-aminohexyl)-AMP [Mosbach, *Methods in Enzymology* 34:230(1974)] in 20 ml of water adjusted to pH 10 with sodium hydroxide. After 1 hour the cold solution was diluted to 2 liters with distilled water and applied to a column of DEAE cellulose (5×100 cm, bicarbonate form). The column was washed with 2 liters of water, then eluted with a linear gradient of 8 liters of water to 8 liters of 0.5M aqueous triethylammonium bicarbonate. Twenty ml fractions were collected.

Fractions 370 to 415 were combined and evaporated. The residue was taken up in 50 ml of distilled water, filtered, and the filtrate lyopholized to give 1.17 g (48% yield) of $N^6$-{6-[6-(1,3-dimethylxanthyl-9)hexanamido]hexyl}adenosine monophosphate as a glassy, white solid.

Analysis: Calculated for $C_{29}H_{43}N_{10}PO_{10} \cdot N(C_2H_5)_3$: C, 51.02; H, 7.10; N, 18.70; P, 3.76. Found: C, 52.18; H, 8.29; N, 17.69; P, 3.31.

$^1$H NMR Spectrum (D$_2$O): $\delta$8.54 (s, 1H) and $\delta$8.14 (s, 1H), adenine aromatic protons; $\delta$7.65 (s, 1H), xanthine aromatic proton.

The xanthine AMP conjugate (842 mg, 1 mmol) was dried by repeated evaporation (6×25 ml) from dry dimethylformamide in vacuo. The dry material was dissolved in 5 ml of dry dimethylformamide and stirred under argon while 811 mg (5 mmol) of 1,1′-carbonyl dimidazole was added [Hoard and Ott, J. Amer. Chem. Soc. 87:1785(1965)]. The solution was stirred for 4 hours at 25° C. and then 1 ml of absolute methanol was added. After 5 minutes the solution was evaporated uder high vacuum, 10 ml of dry dimethylformamide added, and the process repeated. The resulting oil was dissolved in 5 ml of dry dimethylformamide and added to a dimethylsulfoxide (DMSO) solution of tri-n-octylamine. The resulting mixture was evaporated under high vacuum, 10 ml of dry DMSO added, and the process repeated. The residual oil was taken up in 10 ml of dry DMSO and combined with the previously prepared solution. This combined solution was stirred for 24 hours, then diluted to 2 liters with distilled water and applied to a column of DEAE cellulose (5×60 cm, bicarbonate form). The column was washed with 6 liters of water and then eluted with a linear gradient of 6 liters of water to 6 liters of 0.6M aqueous ammonium acetate solution, pH 5.6. At the end of the gradient, elution was continued with 0.6M ammonium acetate. Twenty two ml fractions were collected.

Fractions 555 to 665 were combined and evaporated in vacuo to 80 ml volume. This was partially desalted on a Bio Gel P2 column (5×120 cm) eluting with water. Desalting was completed by 3 dilutions with water and ultrafiltration through an Amicon UM-05 membrane, and a final chromatography on P2 (5×120 cm) eluting with water. This gave 242 micromoles of the desired FAD-theophylline conjugate.

Analysis: UV Spectrum (H$_2$O, pH 5.3): $\lambda$max 266, 375, 453 nm. $^1$H NMR Spectrum (D$_2$O): $\delta$8.28; 7.83 (2 1H singlet, adenine ring protons); 7.54 (1H singlet, theophylline ring proton); 7.51 (2H singlet, isoalloxazine ring protons); 5.86 (1H doublet, J=3.2 Hz, anomeric H); 3.53 and 3.14 (N-methyls); 2.34 and 2.26 (C-methyls).

EXAMPLE 2

Homogeneous Immunoassay (SLFIA) for Theophylline

A substrate-labeled fluorescent immunoassay (SLFIA) for theophylline was established as follows:

A. Reagents

1. Antibody/Enzyme Reagent—50 mM Bicine buffer [N,N-bis-(2-hydroxyethyl)glycine, Calbiochem-Behring Corp., La Jolla, Calif. USA], pH 8.5, containing 100 Units/liter $\beta$-galactosidase, sufficient antiserum raised against the 9-theophylline immunogen (Example 1, Part B) to decrease fluorescence to 5% of that in the absence of antiserum, and 15.4 mM sodium azide.

2. Conjugate Reagent—5 mM formate buffer, pH 3.5, containing 0.83 $\mu$M (micromolar) $\beta$GU-theophylline (Example 1, Part C) and 15.4 $\mu$M sodium azide.

3. Theophylline Standards—USP-NF Reference Standard theophylline added to normal human serum; diluted 51-fold with 50 mM Bicine buffer, pH 8.5, containing 15.4 $\mu$M sodium azide.

B. Assay Method

To 3 ml volumes of the Antibody/Enzyme Reagent in cuvettes were added 100 $\mu$l (microliters) of the diluted Theophylline Standards. Then to begin the reaction, 100 $\mu$l of the Conjugate Reagent was added to each cuvette with mixing. After 20 minutes the fluorescence intensity was measured in each cuvette (excitation 400 nm, emission 450 nm).

C. Results

Performance of the assay yielded the following results:

| Theophylline ($\mu$g/ml) | Normalized Fluorescence Units |
| --- | --- |
| 0 | 18.5 |
| 10 | 41.0 |
| 20 | 61.0 |
| 30 | 77.0 |
| 40 | 90.0 |

Cross-reactivity studies were performed using antiserum from five different rabbits. Cross-reactivity was defined as the concentration of the compound tested in $\mu$g/ml (micrograms per milliliter) required to produce a 20% increase in the measured theophylline value of a mid-range control (15 $\mu$g/ml). The results were as follows:

| Compound | Cross-Reactivity | | | | |
| --- | --- | --- | --- | --- | --- |
| | #1 | #2 | #3 | #4 | #5 |
| caffeine | >100 | >100 | >100 | >100 | 76 |
| 3,7-dimethylxanthine | <400 | >400 | >400 | >400 | >400 |
| 1,3-dimethyluric acid | <500 | >500 | >500 | >500 | >500 |
| 1,3,7-trimethyluric acid | ~200 | >200 | >200 | >200 | ~100 |
| 1,7-dimethylxanthine | >200 | >200 | >200 | >200 | <200 |
| 8-chlorotheophylline | 6 | 9 | 10 | >10 | 5 |
| 1-methylxanthine | >50 | >50 | >50 | 22 | 24 |

Further cross-reactivity studies were performed to compare the 9-theophylline antiserum of the present invention to 8-theophylline antiserum (U.S. Pat. No. 4,279,992). The results were as follows:

| Compound | Cross-Reactivity | |
| --- | --- | --- |
| | 8-position | 9-position |
| caffeine | 8 | 226 |
| 1,3-dimethyl uric acid | 20 | >2000 |
| 1,7-dimethylxanthine | 100 | 557 |
| 1,3,7-trimethyl uric acid | 130 | 399 |
| 3,7-dimethylxanthine | 200 | 1656 |
| 3-methylxanthine | >100 | 756 |
| 3-methyl uric acid | >100 | >2000 |
| 1-methyl uric acid | >100 | >2000 |
| hypoxanthine | >10,000 | >2000 |
| urea | >10,000 | >5000 |
| xanthine | >10,000 | >2000 |

The data indicate a significant decrease in cross-reactivity with the compounds caffeine, 1,3-dimethyl uric acid, 1,7-dimethylxanthine, etc., by moving from the 8-position to the 9-position in preparing the theophylline immunogen.

EXAMPLE 3

Homogeneous Immunoassay (PGLIA) for Theophylline

A prosthetic group-labeled immunoassay (PGLIA) for theophylline was established as follows:

A. Reagents

Reagent A—0.1M sodium phosphate buffer (pH 7.0), 1.05% bovine serum albumin, 0.105M glucose, 63 µg/ml peroxidase, 2.1 mM sodium 3,5-dichloro-2-hydroxybenzene sulfonate, in water.

Reagent B—1 µM FAD-theophylline conjugate (Example 1, Part D) in 50 mM sodium phosphate buffer (pH 7.0).

Reagent C—4 µM apoglucose oxidase, 8 mM 4-aminoantipyrine, 30% glycerol, in 0.1M phosphate buffer (pH 7.0).

Reagent D—theophylline (40 µg/ml) in pooled human serum.

Reagent E—Antiserum to theophylline diluted 10-fold in 0.1M sodium phosphate buffer (pH 7.0).

B. Assay Method

Into separate corners of a series of reaction cuvettes were dispensed 10 µl of Reagent B, 100 µl of Reagent C, varying volumes of Reagent D (as set out in the results table below) and 25 µl of Reagent E. Reagent A (1.9 ml) was then added to each cuvette with rapid mixing followed by a 5 minute incubation at 25° C. The absorbance at 520 nm was then measured for each cuvette.

C. Results

The results were as follows (averages of duplicate runs):

| volume added (µl) | Theophylline concentration (ng/ml) | Absorbance (520 nm) |
|---|---|---|
| 0 | 0 | 0.184 |
| 0.5 | 10 | 0.233 |
| 1.0 | 20 | 0.326 |
| 2.5 | 50 | 0.470 |
| 5 | 100 | 0.524 |
| 10 | 200 | 0.578 |

Thus, an assay was provided for determining theophylline using the reagents of the present invention.

What is claimed is:

1. In an immunoassay method for determining theophylline in a test sample, wherein the test sample is combined with an antibody to theophylline and with a labeled form of theophylline or a binding analog of theophylline, and wherein the relative amount of the labeled reagent that becomes bound to the antibody is determined, the improvement which comprises employing as the antibody to theophylline an antibody prepared against an immunogen comprising theophylline covalently linked at its 9-position to an immunogenic carrier material.

2. The method of claim 1 wherein said immunogen is of the formula:

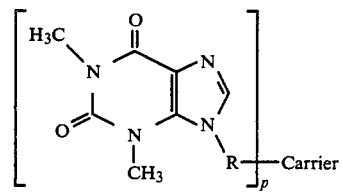

wherein R is a chain comprising between 1 and 20 atoms excluding hydrogen, Carrier is said immunogenic carrier material, and p is on the average from 1 to about 50.

3. The method of claim 2 wherein said carrier material is a protein or polypeptide.

4. The method of claim 1 wherein the labeled reagent has a detectable property which is altered when bound with said antibody.

5. In reagent means for determining theophylline by immunoassay comprising an antibody to theophylline and a labeled form of theophylline or a binding analog of theophylline, the improvement which comprises employing as the antibody to theophylline an antibody prepared against an immunogen comprising theophylline covalently linked at its 9-position to an immunogenic carrier material.

6. The reagent means of claim 5 wherein said immunogen is of the formula:

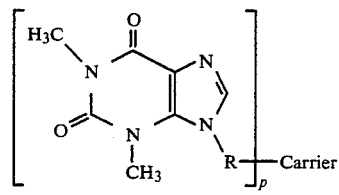

wherein R is a chain comprising between 1 and 20 atoms, excluding hydrogen, Carrier is said immunogenic carrier material, and p is on the average from 1 to about 50.

7. The reagent means of claim 6 wherein said carrier material is a protein or polypeptide.

8. The reagent means of claim 5 wherein the labeled reagent has a detectable property which is altered when bound with said antibody.

9. The reagent means of claim 5 in the form of a test kit wherein said antibody and labeled reagent are held in separate containers.

10. The reagent means of claim 8 in the form of a test device comprising a solid carrier member incorporated with said antibody to theophylline and said labeled form of theophylline or binding analog of theophylline.

11. The reagent means of claim 5 wherein said labeled reagent has the formula:

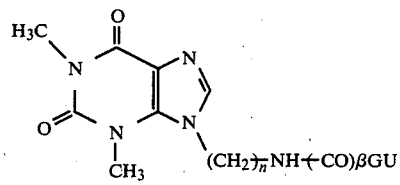
wherein ─(CO)βGU is
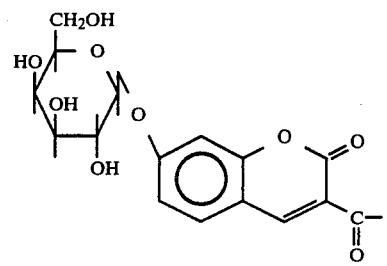
and n is an integer from 1 through 10.
12. The reagent means of claim 5 wherein said labeled reagent has the formula:
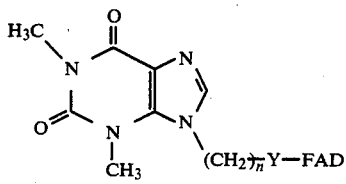
wherein FAD is flavin adenine dinucleotide or a derivative thereof, Y is an amide group, and n is an integer from 1 through 10.
* * * * *